(12) United States Patent
Kim et al.

(10) Patent No.: US 9,824,783 B2
(45) Date of Patent: Nov. 21, 2017

(54) X-RAY SHIELDING APPARATUS AND METHOD

(71) Applicant: Korea Institute of Geoscience and Mineral Resources, Daejeon (KR)

(72) Inventors: Kyeong Ja Kim, Daejeon (KR); Seung Ryeol Lee, Daejeon (KR); Yi Re Choi, Gyeongsangnam-do (KR); Eung Seok Yi, Daejeon (KR)

(73) Assignee: KOREA INSTITUTE OF GEOSCIENCE AND MINERAL RESOURCES, Daejeon (KR)

( * ) Notice: Subject to any disclaimer, the term of this patent is extended or adjusted under 35 U.S.C. 154(b) by 245 days.

(21) Appl. No.: 14/410,628

(22) PCT Filed: Dec. 3, 2014

(86) PCT No.: PCT/KR2014/012184
§ 371 (c)(1),
(2) Date: Dec. 23, 2014

(87) PCT Pub. No.: WO2016/088926
PCT Pub. Date: Jun. 9, 2016

(65) Prior Publication Data
US 2016/0314862 A1    Oct. 27, 2016

(30) Foreign Application Priority Data
Dec. 3, 2014  (KR) .................. 10-2014-0172271

(51) Int. Cl.
*H01J 35/16* (2006.01)
*G21F 3/00* (2006.01)
(Continued)

(52) U.S. Cl.
CPC ............ *G21F 3/00* (2013.01); *G01N 23/223* (2013.01); *G21F 5/06* (2013.01)

(58) Field of Classification Search
CPC .. G01N 23/223; G01N 2223/076; G21F 3/00; G21F 5/06; G21F 7/02; G21F 7/04; G21F 1/12; G21F 1/02; G21F 1/106; G21F 3/025; G21F 3/035; G21D 1/003; G21Y 2002/301; G21Y 2002/302; G21Y 2002/304; G21Y 2004/20; G21Y 2004/30;
(Continued)

(56) References Cited

U.S. PATENT DOCUMENTS

| 8,540,425 B2* | 9/2013 | Nielsen Groot | A61B 6/107 378/203 |
| 2010/0111266 A1* | 5/2010 | Kuhnmuench | G21F 7/005 378/203 |

FOREIGN PATENT DOCUMENTS

| JP | 2003245269 A | * 9/2003 |
| KR | 10-20010039201 A | 5/2001 |

(Continued)

*Primary Examiner* — Irakli Kiknadze
(74) *Attorney, Agent, or Firm* — Dentons US LLP

(57) ABSTRACT

The invention generally relates to a radiation shielding apparatus that includes a shielding box unit into which a radiation generating device is inserted, a locking unit disposed on an outside of the shielding box unit, an operation display unit disposed on the outside of the shielding box unit to display a locked state of the locking unit, and a control unit for controlling an operation of each of the radiation generating device and the operation display unit.

6 Claims, 7 Drawing Sheets

(51) Int. Cl.
*G01N 23/223* (2006.01)
*G21F 5/06* (2006.01)

(58) Field of Classification Search
CPC ....... H01L 2924/00014; H01L 2924/00; H01L
2224/48247; H01L 2224/49171; H01L
2224/48227; H01L 2224/49175; H01L
2224/48091; H01L 2224/05599; H01L
2224/85399; H01L 2224/45015; H01L
2224/45099; H01L 23/552; H01L
2924/207; A61B 6/107; A61B 6/4423;
A61B 6/4441; A61B 6/035; A61B 6/487;
A61B 6/589; A61B 6/032; A61B 6/502;
A61B 6/4405; A61B 6/4429; A61B
6/037; A61B 6/10; A61B 6/467; A61B
6/508; A61B 6/583; A61B 46/10; A61B
5/055; A61B 6/04
USPC ............................................ 378/42, 44, 203
See application file for complete search history.

(56) References Cited

FOREIGN PATENT DOCUMENTS

| KR | 10-20060135132 A | 12/2006 |
|---|---|---|
| KR | 10-1185743 B1 | 9/2012 |
| KR | 101185743 B1 * | 9/2012 |
| KR | 10-1433144 B1 | 8/2014 |

* cited by examiner

X-RAY SHIELDING APPARATUS AND METHOD

CROSS-REFERENCE TO RELATED APPLICATION

This application is the Section 371 National Stage of PCT/KR2014/012184 filed on Dec. 3, 2014, the entirety of which is incorporated herein by reference to the extent permitted by law. This application claims the benefit of priority to Korean Patent Application No. KR 10-2014-0172271, filed Dec. 3, 2014 the entirety of which is incorporated herein by reference to the extent permitted by law.

BACKGROUND OF THE INVENTION

The present invention relates to an apparatus and method for shielding X-rays that are generated when a sample to be measured is analyzed by using radiation, and more particularly, to a radiation shielding apparatus and method for preventing the radiation from leaking from a radiation fluorescent analyzing device.

In general, radiation fluorescent analyzing device is a kind of non-destructive analyzing device for obtaining information in regard to atom and electron structures such as industrial materials, i.e., semiconductor materials, catalysts, and amorphous materials.

Typically, the radiation fluorescent analyzing apparatus usually uses X-rays that are a kind of radiation. Hereinafter, the X-ray fluorescent analyzing device will be described in detail as an example.

In the X-ray fluorescent analyzing device, the X-rays are irradiated to a sample, and then energy of a fluorescent photon that is generated from the sample is detected to analyze the sample.

That is, the X-rays used for the X-ray fluorescent analysis correspond to fluorescent X-rays having energy of about 25 KeV or less. Here, energy of the fluorescent photon that is radiated from an object to be measured (hereinafter, referred to as a "measurement object") to which the X-rays are absorbed may be detected to measure elementary composition of the measurement object.

The principle of X-ray generation in an X-ray tube is as follows. Broad-band x-rays are generated to correspond to an anode voltage of first fluorescent x-rays that are generated from a target in the tube. Usually, since silver (Ag) generates specific radiation of about 24 KeV or less, when an anode voltage of about 35 KVp is applied to the silver (Ag), X-rays of about 3 KeV to about 35 KeV may be generated.

Also, the generated X-rays travel at an angle of about 180° with respect to an anode surface. Here, the X-rays are radiated in the form of electromagnetic waves with respect to a reflection angle corresponding to an incident angle of the incident electron beam to travel in parabolic distribution.

The generated X-rays may be shielded except for a portion thereof toward the sample by a collimator. Here, only a portion of the X-rays may be transmitted to correspond to an area to be irradiated of the sample. Thus, the X-rays are not scattered by mechanisms around the sample to unaffect the measurement.

The X-rays incident into the sample dislodge an orbital electron of each of the elements composing the sample or excites an orbital electron of each of the elements composing the sample to a high energy level, thereby losing energy thereof. Here, X-rays having a specific wavelength generated due to energy differences between orbits of the electron while the electron is transited from a relatively high orbit to a relatively low orbit is radiated, and the X-rays are called characteristic X-rays.

Also, the energy of the generated characteristic X-rays is classified by an element, distribution of the energy generated from the electron orbits K, L, and M is measured in a spectrum manner to quantitatively and qualitatively measure the measurement object.

Thus, the radiation fluorescent analyzing device for quantitatively and qualitatively measuring the measurement object by using the radiation such as the X-rays needs a shielding apparatus that is capable of efficiently shielding the radiation.

An example of the X-ray shielding apparatus according to the related art is disclosed in Korean Patent Application No. 10-2012-0026833, titled "Fluorescent X-ray Analyzing Shielding Apparatus".

According to the related art disclosed in Korean Patent Application No. 10-2012-0026833, there is provided a fluorescent X-ray analyzing shielding apparatus including: a shielding box; a first door slid on the shielding box; a sample holder disposed on a lower end of the first door, wherein the shielding box includes an acryl plate, a lead-glass plate formed on the outside of the acryl plate, and an aluminum plate formed on the outside of the lead-glass plate, a partition wall is disposed in the shielding box, and a second door is openably disposed on the partition wall.

According to the related art, fluorescent X-rays generated by irradiating X-rays that are radiated from a radioactive isotope onto the sample are measured by an X-ray spectrometer. Then, a frequency of an energy area of each of components by analyzing a spectrum is used to obtain a component content in the irradiated sample. Thus, the fluorescent X-ray analyzing shielding apparatus is provided so as to perform the analyzing process within the safe shielding box. The sample is seated in the fluorescent X-ray analyzing shielding apparatus, and the X-ray fluorescent analyzing device operates only in a state where all doors are closed to prevent the radiation from leaking to the outside. Also, a distance between the sample and a radiation source irradiating the radiation onto the sample may be adjusted in a state where the shielding box is closed to easily analyze the sample.

On the other hand, according to the related art, it is difficult to recognize operation states of various devices in the shielding box from the outside, and thus a user may not easily recognize whether the radiation leaks from the outside.

Also, in order to operate the radiation generating device within the shielding box, a power supply line has to be connected to the radiation generating device. Thus, the shielding box needs a line through-hole. Therefore, the radiation may leak through the through hole.

SUMMARY OF THE INVENTION

The present invention provides a radiation shielding apparatus having a function for detecting whether an opening portion thereof is completely coupled to a cover to display the detected result when the opening portion of the shielding apparatus is coupled to the cover and a radiation shielding method.

The present invention also provides a radiation shielding apparatus having a function for preventing radiation from leaking through a through-hole defined in a shielding box, through which a line passes and a radiation shielding method.

The present invention also provides a radiation shielding apparatus having a radiation leakage display function at the outside of a shielding box to detect whether radiation leaks from the outside of the shielding box and a radiation shielding method.

Embodiments of the present invention provide a radiation shielding apparatus including: a shielding box unit into which a radiation generating device is inserted; a locking unit disposed on an outside of the shielding box unit; an operation display unit disposed on the outside of the shielding box unit to display a locked state of the locking unit; and a control unit for controlling an operation of each of the radiation generating device and the operation display unit.

Also, the shielding box unit may include: a cover; and a shielding box locked with the cover by the locking unit and having a sidewall and a bottom surface.

Also, the shielding box may further include vibration detection sensor connected to the control unit and disposed on an outside of a front sidewall thereof to detect vibration.

Also, the shielding box may further include a radiation detection sensor connected to the control unit and disposed therein to detect radiation.

The shielding box may further include: a sample holder therein; a through-hole defined in one side of the sidewall to allow a line to pass therethrough; and a line guiding unit disposed in front of the through-hole and having two plates, each of which is manufactured with two layers in which lead is added on the inside of an aluminum plate, at a front side of the through-hole, wherein the two plate are bent so that the two plates are disposed in parallel to be spaced a predetermined distance apart from each other, thereby preventing the radiation from leaking.

The locking unit may include: a cover locking part disposed on an outer surface of the cover; and a locking detection part disposed on the shielding box unit to detect the locked state of the shielding box unit when the shielding box is locked with the cover by the cover locking part.

The locking detection part may include: a push part disposed on the cover; and an interlock disposed on the shielding box to correspond to the push part to detect the push part, thereby outputting a locking detection signal.

The cover locking part may include: a hook disposed on the cover; and a buckle coupled to the hook and disposed to correspond to the hook of the shielding box.

In other embodiments of the present invention, a method of shielding radiation by using a radiation shielding apparatus into which a radiation generating device is inserted includes: a locking determination process for determining a locked state of a shielding box unit; a locking display process for turning on an operation display unit when it is detected that the shielding box unit is locked through the locking determination process; a power supply process that is simultaneously performed together with the locking determination process to supply power to the radiation generating device when the shielding box unit is locked; a radiation irradiating process for operating the radiation generating device by using the power supplied through the power supply process to generate radiation, thereby irradiating the generated radiation to a sample holder; and a sample analyzing process for analyzing a sample of the sample holder by using the radiation irradiated through the radiation irradiating process.

The locking determination process may further include an opening display process for turning off the operation display unit when the shielding box unit is opened.

The radiation irradiating process may include: a radiation generation determination process for determining whether the radiation is generated from the radiation generating device; a radiation non-generation determination process for turning off a lamp of the operation display unit when the radiation is not generated in the radiation generation determination process; and a radiation generation display process for turning on the lamp of the operation display unit when the radiation is generated in the radiation generation determination process.

BRIEF DESCRIPTION OF THE DRAWINGS

The accompanying drawings are included to provide a further understanding of the present invention, and are incorporated in and constitute a part of this specification. The drawings illustrate exemplary embodiments of the present invention and, together with the description, serve to explain principles of the present invention. In the drawings.

DETAILED DESCRIPTION OF THE PRESENTLY PREFERRED EMBODIMENTS

Figure 1:
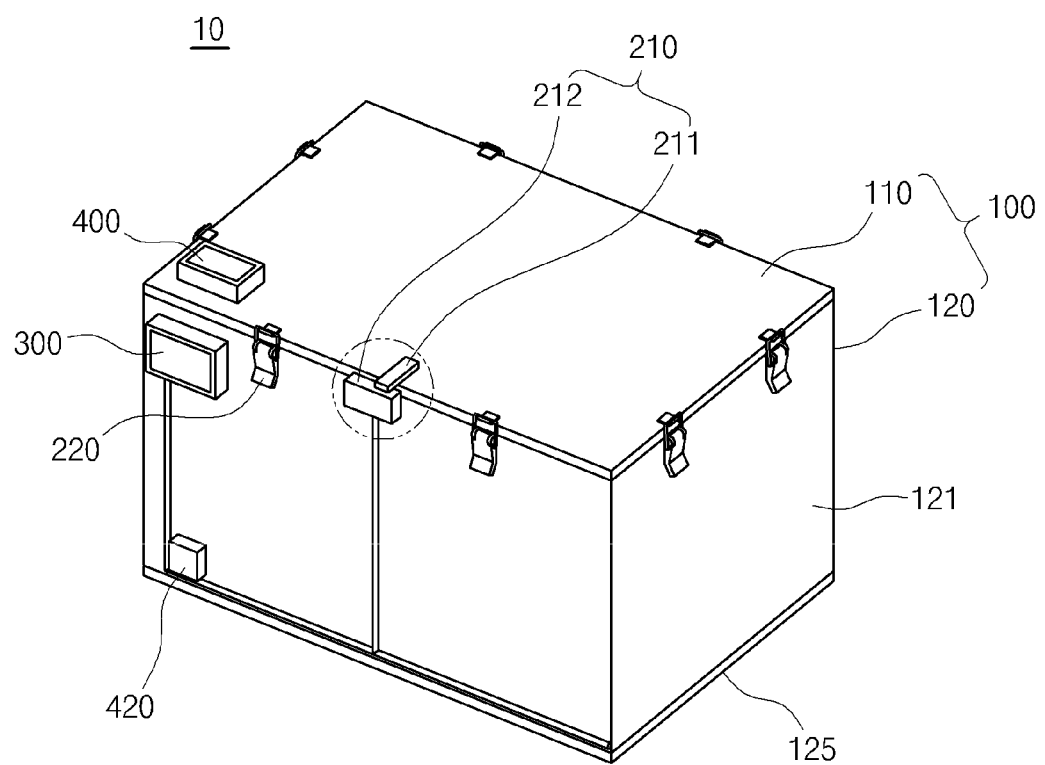
FIG. 1 is a perspective view of a radiation shielding apparatus according to an embodiment of the present invention.

Preferred embodiments of the present invention will be described below in more detail with reference to the accompanying drawings. The present invention may, however, be embodied in different forms and should not be constructed as limited to the embodiments set forth herein. Rather, these embodiments are provided so that this disclosure will be thorough and complete, and will fully convey the scope of the present invention to those skilled in the art. Like reference numerals refer to like elements throughout.

Hereinafter, it will be described about an exemplary embodiment of the present invention in conjunction with the accompanying drawings.

Figure 2:
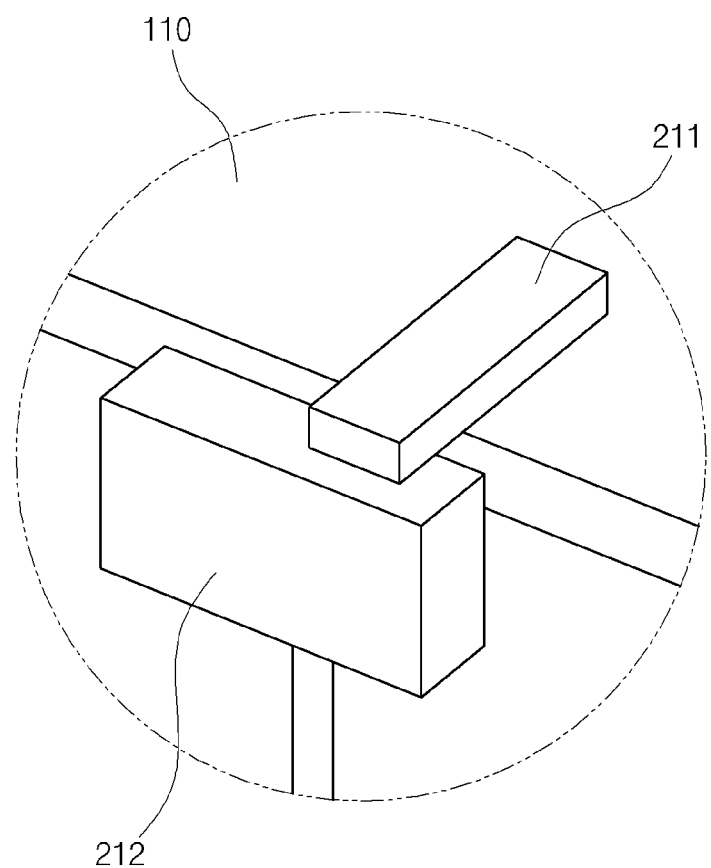
FIG. 2 is a view of a locking detection part of the shielding apparatus according to an embodiment of the present invention.

FIG. 1 is a perspective view of a radiation shielding apparatus according to an embodiment of the present invention, and FIG. 2 is a view of a locking detection part of the shielding apparatus.

As illustrated in FIGS. 1 and 2, the shielding apparatus 10 includes a shielding box unit 100, a locking unit 200, an operation display unit 300, a handle 400, and a vibration detection sensor 420.

A radiation generating device 600 that will be described later is inserted into the shielding box unit 100. The shielding box unit 100 is constituted by a cover 110 and a shielding box 120. The shielding box 120 is constituted by sidewalls 121 and a bottom surface 125. A sample holder 500 that will be described later is disposed in the shielding box 120 to perform a sample analyzing experiment by using an X-ray which is a kind of radiation that is generated from the radiation generating device 600.

The shielding box 120 may have an inside that is coated with lead in thickness of about 0.5 mm. When the lead has a thickness of about 0.5 mm or more, 100% of 35 KeV X-rays may be shield. However, the X-ray generated by the radiation generating device 600 may almost have energy of about 8 KeV. Thus, the shielding box 120 may almost perfectly prevent the X-ray generated from the radiation generating device 600 from leaking to the outside.

Also, each of all surfaces in the shielding box 120 may be formed of an acryl plastic sheet having a thickness of about 1 mm or more so as to prevent the sample from contacting the lead.

The cover 110 is coupled to an opening part of the shielding box 120 to prevent the X-ray from leaking to the outside. Each of the cover 110 and the shielding box 120 may be manufactured by successively stacking aluminum, lead, and acryl layers from the outside.

The locking unit 200 is constituted by the locking detection part 210 and a cover locking part 220.

The locking detection part 210 may include a push part 211 disposed on an upper central portion of the cover 110 and an interlock 212 disposed on an upper central portion of a front sidewall of the shielding box 120 to correspond to the push part 211 so as to detect the push part 211.

The push part 211 may be formed of an aluminum material. The push part 211 may contact or face the interlock 212 when the cover 110 is completely coupled to the shielding box 120, and thus the interlock 212 may detects a locked state.

The interlock 212 may include a detection switch (not shown) that directly contacts the push part 211 In order to continuously push the detection switch, the cover 110 and the shielding box 120 may be locked with enough power by the cover locking part 220.

The cover locking part 220 may include a plurality of hooks 221 each of which is formed of a metal material and is disposed on a side surface of the cover 110 and a plurality of buckles 222 each of which is formed of a metal material and is disposed on an upper portion of the sidewall 121 of the shielding box 120 to correspond to the hook 221.

When the shielding box unit 100 is opened, the interlock 212 prevents power from being supplied into the radiation generating device 600 to close a shutter 610 of the radiation generating device 600.

That is, when the cover 110 of the shielding box 120 is opened, the interlock 212 may detect that the cover 110 is opened to transfer a signal to a control unit 1000 that will be described later. Then, the control unit 1000 may prevent the power from being supplied into the radiation generating device 600 to close the shutter 610 of the radiation generating device 600.

The operation display unit 300 may use a light emitting diode (LED) lamp as a light emitting source. The operation display unit 300 is mounted on an upper portion of an outer front sidewall 121 of the shielding box 120 to turn the light emitting source on so that the locked state of the radiation shielding apparatus 10 or whether the radiation leaks may be recognized from the outside.

Thus, when the power is supplied to operate the radiation generating device 600, or when the supply of the power is blocked to stop the operation of the radiation generating device 600, the operation display unit 300 turns the light emitting source on or off to display the operation state.

That is, when the radiation generating device 600 operates and is heated, the operation display unit 300 is turned on, and when the radiation generating device 600 stops in operation and is not heated, the operation display unit 300 is turned off.

Thus, an experimenter may recognize whether the X-ray is generated or whether the X-ray leaks from the outside without opening the shielding box unit 100.

The handle 400 may be disposed on an upper central portion of the cover 110 in consideration of portability of the radiation shielding apparatus 10.

The vibration detection sensor 420 is disposed at the outside of the front sidewall 121 of the shielding box 120 and connected to the control unit 1000. When the vibration detection sensor 420 detects that the shielding box unit 100 wobbles due to an earthquake or movement thereof, the control unit 1000 may prevent the power from being supplied into the shielding box unit 100.

Figure 3:
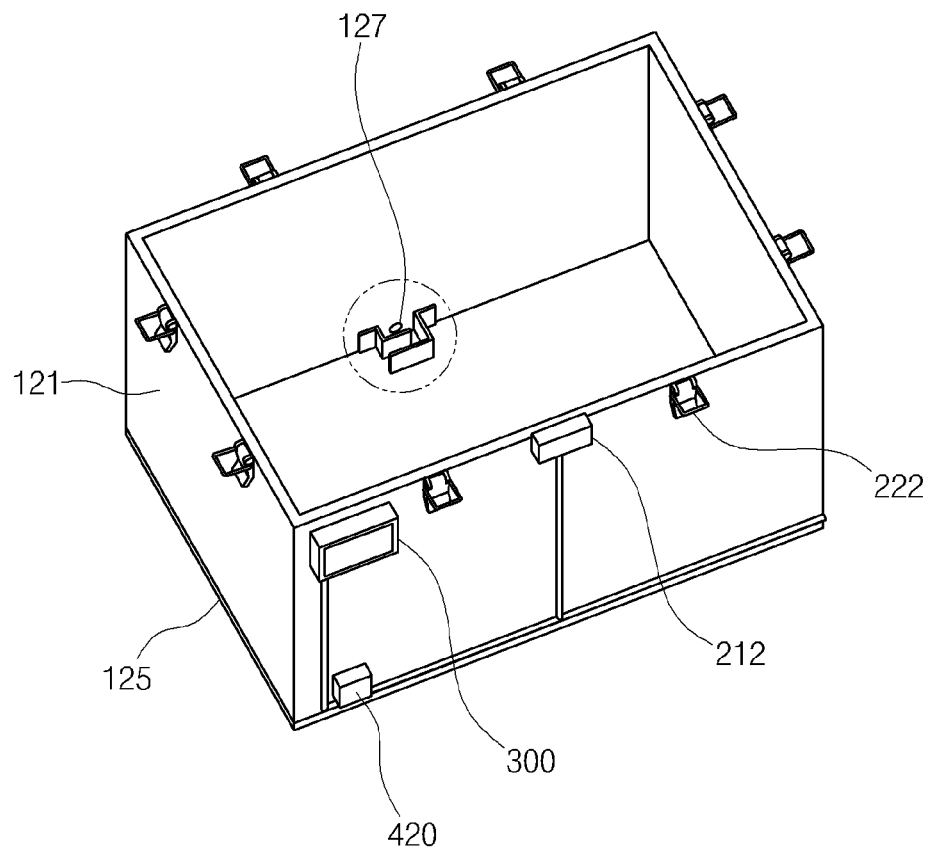
FIG. 3 is a view of a through-hole of the shielding apparatus according to an embodiment of the present invention.

FIG. 3 is a view of a through-hole of the shielding apparatus.

As illustrated in FIG. 3, a through-hole 127 is defined in the sidewall 121 of the shielding box 11.

Lines or power lines for connecting the control unit 1000 to the radiation generating device 600 or various devices may pass through the through-hole 127.

Figure 4:
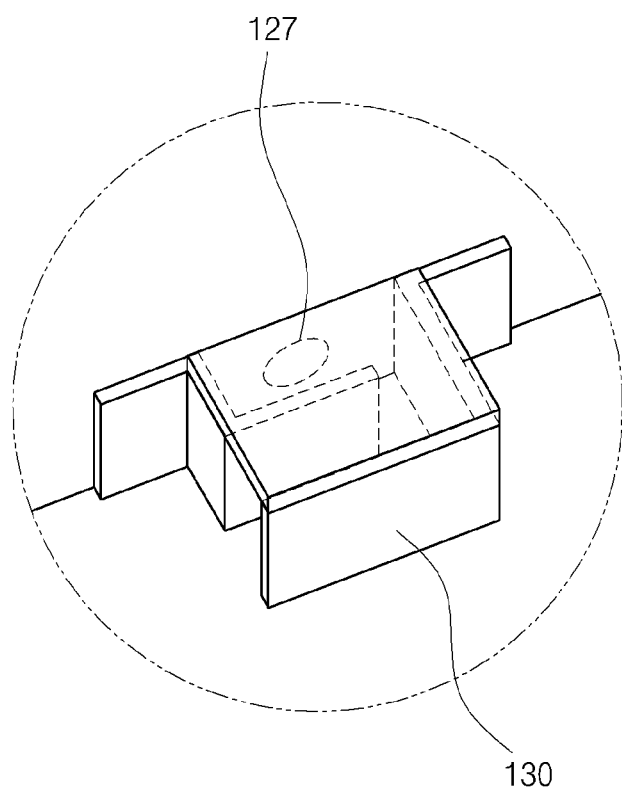
FIG. 4 is a view of a line guiding unit of the shielding apparatus according to an embodiment of the present invention.

FIG. 4 is a view of a line guiding unit of the shielding apparatus.

As illustrated in FIG. 4, the shielding box 120 includes a line guiding unit 130 therein.

In the line guiding unit 130, two plates each of which is manufactured with two layers in which lead is added on an inside of an aluminum plate, at a front of the through-hole 127. Here, the two plates are bent so that the two plates are disposed in parallel to be spaced a predetermined distance apart from each other.

The line guiding unit 130 may allow the lines or power lines for connecting the control unit 1000 to the radiation generating device 600 to pass through the through-hole 127. Also, the line guiding unit 130 may shield the radiation inside the shielding box 120 to prevent the radiation such as the X-ray from leaking through the through-hole 127.

That is, although the line guiding unit 130 allows the line to pass therethrough, the line guiding unit 130 may prevent the X-ray having linear property from leaking to the outside.

Figure 5:
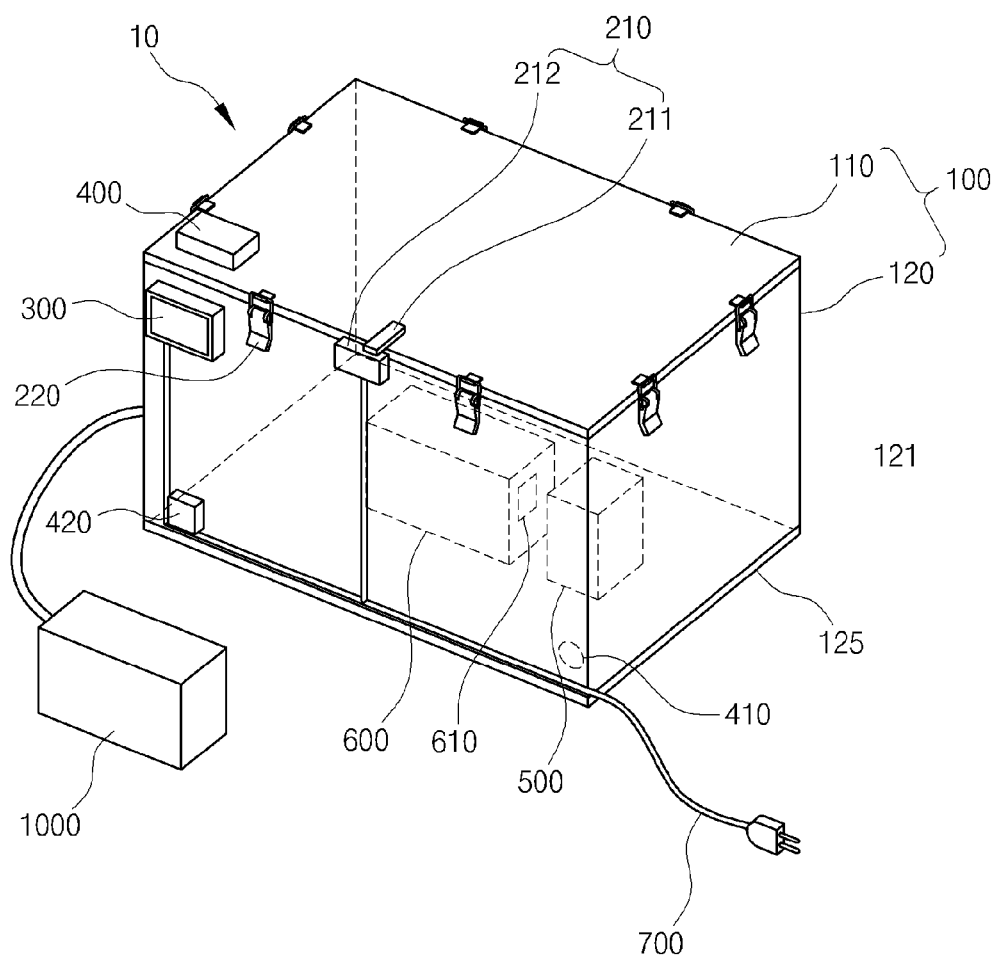
FIG. 5 is a view illustrating an example applied according to an embodiment of the present invention.

FIG. 5 is a view illustrating an example applied according to an embodiment of the present invention.

As illustrated in FIG. 5, the radiation shielding apparatus 10 includes the radiation generating device 600, the shutter 610, a radiation detection sensor 410, the sample holder 500, and a power source line 700.

When the power is supplied through the power source line 700, the radiation generating device 600 may open the shutter 610 to irradiate the X-ray to the sample holder 500 formed of the acryl material and to which the sample is inserted, thereby allowing the control unit 1000 to analyze the sample.

The above-described various devices may be controlled by the control unit 1000. That is, the control unit 1000 detects whether the interlock 212 contacts to determine whether the X-ray in the shielding box unit 100 leaks, thereby operating the shutter 610 of the radiation generating device 600 or controlling the turn-on/off of the operation display unit 300.

Also, since the radiation detection sensor 410 connected to the control unit 1000 is disposed in the shielding box 120, radiation detection within the shield box 120 may be possible.

Figure 6:
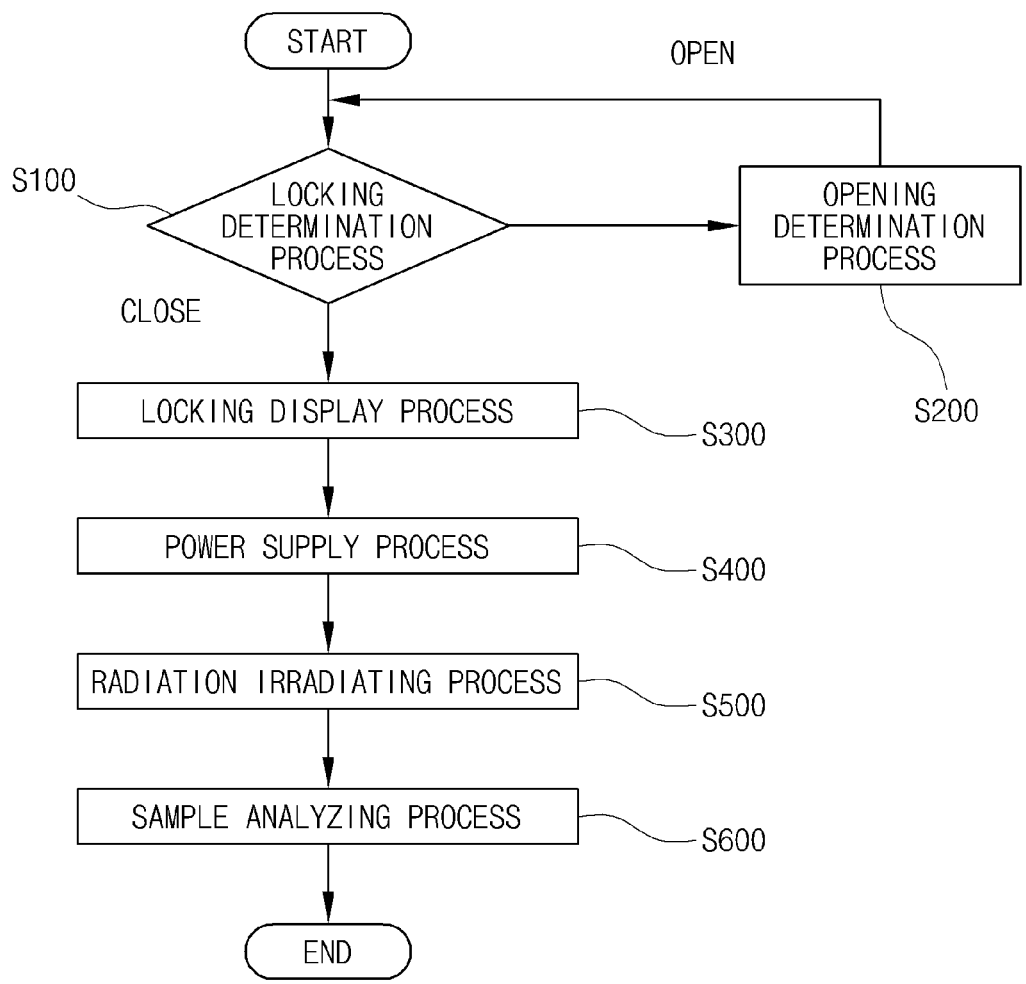
FIG. 6 is a flowchart illustrating a processing process of a radiation shielding method according to an embodiment of the present invention.
Figure 7:
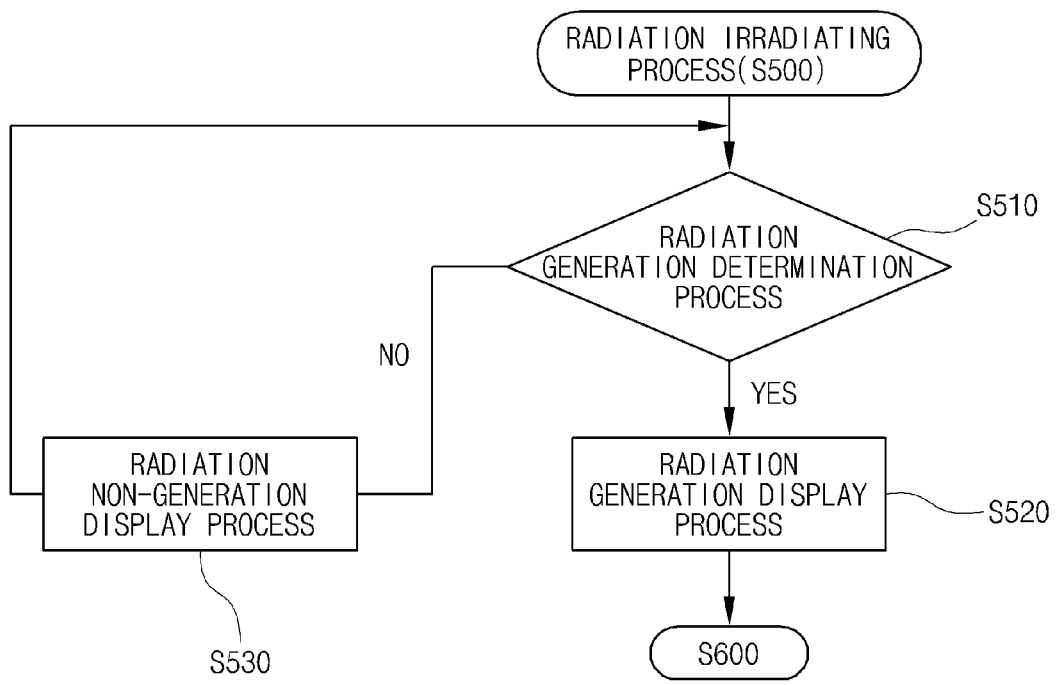
FIG. 7 is a flowchart illustrating a detailed processing process of radiation irradiating process (S500) of the processing process of FIG. 6 according to an embodiment of the invention.

FIG. 6 is a flowchart illustrating a processing process of a radiation shielding method according to an embodiment of the present invention, and FIG. 7 is a flowchart illustrating a detailed processing process of radiation irradiating process (S500) of the processing process of FIG. 6.

As illustrated in FIGS. 6 and 7, the method of shielding the radiation includes a locking determination process (S100), an opening display process (S200), a locking display process (S300), a power supply process (S400), a radiation irradiating process (S500), and a sample analyzing process (S600).

In the locking determination process (S100), the control unit 1000 determines whether the cover 110 is locked with the shielding box 120 by the cover locking part 220 through the locking detection part 210.

In the opening display process (S200), the control unit 1000 detects that the cover locking part 220 is opened through the locking detection part 210 to turn off the LED lamp of the operation display unit 300.

In the locking display process (S300), the control unit 1000 detects that the cover locking part 220 is locked through the locking detection part 210 to turn on the LED lamp of the operation display unit 300.

In the power supply process (S400), when the control unit 1000 detects that the shielding box unit 100 is locked through the locking detection part 210, the power is supplied into the radiation generating device 600. The power supply process (S400) and the locking determination process (S300) are performed at the same time.

In the radiation irradiating process (S500), the radiation generating device 600 receiving the power through the power supply process (S400) opens the shutter 610 to irradiate the radiation to the sample holder 500.

In detail, as illustrated in FIG. 9, the radiation irradiating process (S500) includes a radiation generation determination process (S510), a radiation generation display process (S520), a radiation non-generation display process (S530), and the sample analyzing process (S600).

In the radiation generation determination process (S510), the control unit 1000 detects whether the radiation is generated in the shielding box 120 by using the radiation detection sensor 410.

In the radiation generation display process (S520), when the control unit 1000 detects that the radiation is generated in the shielding box 120, the lamp of the operation display unit 300 is turned on.

In the radiation non-generation display process (S530), when the radiation is not generated, and the power is blocked, the control unit 1000 closes the shutter 610 of the radiation generating device 600 to turn off the lamp of the operation display unit 300.

Referring again to FIG. 6, in the sample analyzing process (S600), the control unit 1000 detects energy of fluorescent X-rays generated from the sample after the radiation is irradiated to the sample holder 500 in the radiation irradiating process (500) to analyze the sample.

According to the present invention, when the opening portion of the shielding apparatus is coupled to the cover, the shielding apparatus may detect and display whether the opening portion is completely coupled to the cover, thereby easily recognizing whether the radiation leaks.

Also, the shielding apparatus may have the function for preventing the radiation from leaking through the through-hole that is defined in a portion of the shielding box through which the line passes to safely effectively shield the radiation.

Also, the shielding apparatus may have the radiation leakage display function at the outside of the shielding box to detect whether the radiation leaks from the outside of the shielding apparatus, thereby recognizing whether the radiation leaks without opening the shielding apparatus.

Although a preferred embodiment of the present invention has been disclosed, various changes and modifications may be made thereto by one skilled in the art without departing from the scope and spirit of the invention as set forth in the appended claims. It is also understood that the terms used herein are merely descriptive, rather than limiting, and that various changes may be made without departing from the scope and spirit of the invention.

What is claimed is:

1. A radiation shielding apparatus comprising:
   a shielding box unit into which a radiation generating device is inserted;
   a locking unit disposed on an outside of the shielding box unit;
   an operation display unit disposed on the outside of the shielding box unit to display a locked state of the locking unit; and
   a control unit for controlling an operation of each of the radiation generating device and the operation display unit,
   wherein, the shielding box unit comprises
   (a) a cover,
   (b) a shielding box locked with the cover by the locking unit and having a sidewall and a bottom surface,
   (c) a sample holder therein,
   (d) a through-hole defined in one side of the sidewall to allow a line to pass therethrough,
   (e) a line guiding unit disposed in front of the through-hole and having a first plate and a second plate, each of which is manufactured with two layers in which lead is added on the inside of an aluminum plate, at a front side of the through-hole, and
   (f) the first plate is bent so that a bent portion of the first plate is disposed in front of the through-hole and the second plate is bent so that a bent portion of the second plate is disposed in front of the through-hole, and
   (g) the bent portion of the first plate and the bent portion of the second plate are disposed in parallel and spaced a predetermined distance apart from each other, thereby preventing the radiation from leaking through the through-hole.

2. The radiation shielding apparatus of claim 1, wherein the shielding box further comprises a vibration detection sensor connected to the control unit and disposed on an outside of a front sidewall thereof to detect vibration.

3. The radiation shielding apparatus of claim 1, wherein the shielding box further comprises a radiation detection sensor connected to the control unit and disposed therein to detect radiation.

4. The radiation shielding apparatus of claim 1, wherein the locking unit comprises:
   a cover locking part disposed on an outer surface of the cover; and
   a locking detection part disposed on the shielding box unit to detect the locked state of the shielding box unit when the shielding box is locked with the cover by the cover locking part.

5. The radiation shielding apparatus of claim 4, wherein the locking detection part comprises:

a push part disposed on the cover; and an interlock disposed on the shielding box to correspond to the push part to detect the push part, thereby outputting a locking detection signal.

6. The radiation shielding apparatus of claim 4, wherein the cover locking part comprises:

a hook disposed on the cover; and a buckle coupled to the hook and disposed to correspond to the hook of the shielding box.

* * * * *